United States Patent
Kanungo et al.

(10) Patent No.: US 9,011,594 B1
(45) Date of Patent: Apr. 21, 2015

(54) METHODS FOR FORMING FUNCTIONALIZED CARBON BLACK WITH AMINO-TERMINATED POLYFLUORODIMETHYLSILOXANE FOR PRINTING

(71) Applicant: Xerox Corporation, Norwalk, CT (US)

(72) Inventors: Mandakini Kanungo, Penfield, NY (US); Anton Grigoryev, Webster, NY (US); David J. Gervasi, Pittsford, NY (US); Santokh S. Badesha, Pittsford, NY (US)

(73) Assignee: Xerox Corporation, Norwalk, CT (US)

( * ) Notice: Subject to any disclaimer, the term of this patent is extended or adjusted under 35 U.S.C. 154(b) by 0 days.

(21) Appl. No.: 14/041,508

(22) Filed: Sep. 30, 2013

(51) Int. Cl.
| | |
|---|---|
| C09C 1/44 | (2006.01) |
| C09D 11/00 | (2014.01) |
| B41J 2/47 | (2006.01) |
| B41J 2/17 | (2006.01) |
| C07F 7/18 | (2006.01) |
| B41J 2/435 | (2006.01) |

(52) U.S. Cl.
CPC ... *C07F 7/18* (2013.01); *B41J 2/435* (2013.01)

(58) Field of Classification Search
USPC .................. 347/225, 84; 106/31.6, 472
See application file for complete search history.

(56) References Cited

U.S. PATENT DOCUMENTS

| | | | |
|---|---|---|---|
| 3,489,697 A * | 1/1970 | Brice ............................. 521/89 |
| 6,251,554 B1 * | 6/2001 | Hoffend et al. .......... 430/111.35 |
| 2003/0234840 A1 * | 12/2003 | Pan et al. ........................ 347/84 |
| 2009/0294737 A1 * | 12/2009 | Hoshi ............................. 252/511 |
| 2010/0124661 A1 * | 5/2010 | Moorlag et al. .............. 428/421 |
| 2012/0103212 A1 | 5/2012 | Stowe et al. |
| 2013/0104756 A1 | 5/2013 | Stowe et al. |

* cited by examiner

*Primary Examiner* — Sarah Al Hashimi
(74) *Attorney, Agent, or Firm* — Ronald E. Prass, Jr.; Prass LLP

(57) ABSTRACT

A method for forming functionalized carbon black useful for uniform dispersion in a surface material of a printing system component includes providing carbon black; providing a fluoropolymer having a terminal amino group; and mixing the amino-terminated fluoropolymer and the carbon black, wherein the fluoropolymer is amino-terminated PDMS.

10 Claims, 4 Drawing Sheets

METHODS FOR FORMING FUNCTIONALIZED CARBON BLACK WITH AMINO-TERMINATED POLYFLUORODIMETHYLSILOXANE FOR PRINTING

FIELD OF DISCLOSURE

The disclosure relates to functionalized carbon black fluoropolymers for printing applications. In particular, the disclosure relates to methods for forming functionalized carbon black having amino-terminated polyfluorodimethylsiloxane useful for printing applications such as for use in a surface material of an imaging member of an ink-based digital printing system, or for other printing systems, which may include intermediate transfer member, toner printing, and fusing systems.

BACKGROUND

Ink-based digital printing has emerged to capture the short run and variable data aspect of the offset printing business while still enjoying the print quality and low run cost. Ink-based digital printing is discussed by way of example. Features of ink-based digital printing include: (a) applying dampening fluid to the imaging member, the surface of which may include an infra-red (IR) laser-absorbing material, for example, carbon black in an elastomer, (b) patterning the dampening fluid to form a latent image using a laser imaging system, which may include, for example, an IR laser, (c) developing the latent image with offset ink applied to the imaging member surface, (d) transferring the digital ink image to paper, and (e) fixing the image on a substrate such as paper, card stock, plastic, or another printable medium.

Fluorosilicones are exemplary materials useful for meeting the material requirements of the imaging member surface. Further, the imaging member surface may include IR absorbing material to facilitate digital evaporation of the dampening fluid, and carbon black is an exemplary material useful for a primary IR absorbing material.

Carbon black is known to be characterized by more efficient near infra-red (NIR) absorption than other IR fillers such as black iron oxide and graphite. It is critical that the IR filler is uniformly dispersed in the imaging member surface material. Uniform dispersion of the filler enables increased absorption efficiency, which is required for high speed printing. Also, uniform dispersion of the filler decreases the laser power requirement for adequate evaporation of dampening fluid of the dampening fluid layer disposed on the imaging member surface. Furthermore, if the IR filler is not uniformly distributed in the imaging member surface material, localized non-uniformity of dampening fluid may results, negatively affecting image resolution.

SUMMARY

Conventional carbon black does not uniformly distribute in a fluorosilicone matrix and creates agglomerates of about one to about five microns or higher. A uniform dispersion of carbon black throughout a surface of the imaging plate enables high printing speed, minimized laser power requirements, and better image resolution and is desirable. Methods for forming functionalized carbon black having an amino-terminated fluoropolymer functional group using a coupling agent. In an embodiment, methods of forming functionalized carbon black using, for example, amino-terminated polyfluorodimethylsiloxane are provided that are useful for printing applications for forming imaging member surface material having uniformly dispersed carbon black therein.

Ink-based digital printing systems are discussed by way of example. Inks in accordance with embodiments may also be suitable for other printing systems, such as those that include an intermediate transfer configuration, or toner printing and/or fusing systems.

Exemplary embodiments are described herein. It is envisioned, however, that any system that incorporates features of systems described herein are encompassed by the scope and spirit of the exemplary embodiments.

DETAILED DESCRIPTION

Figure 1:
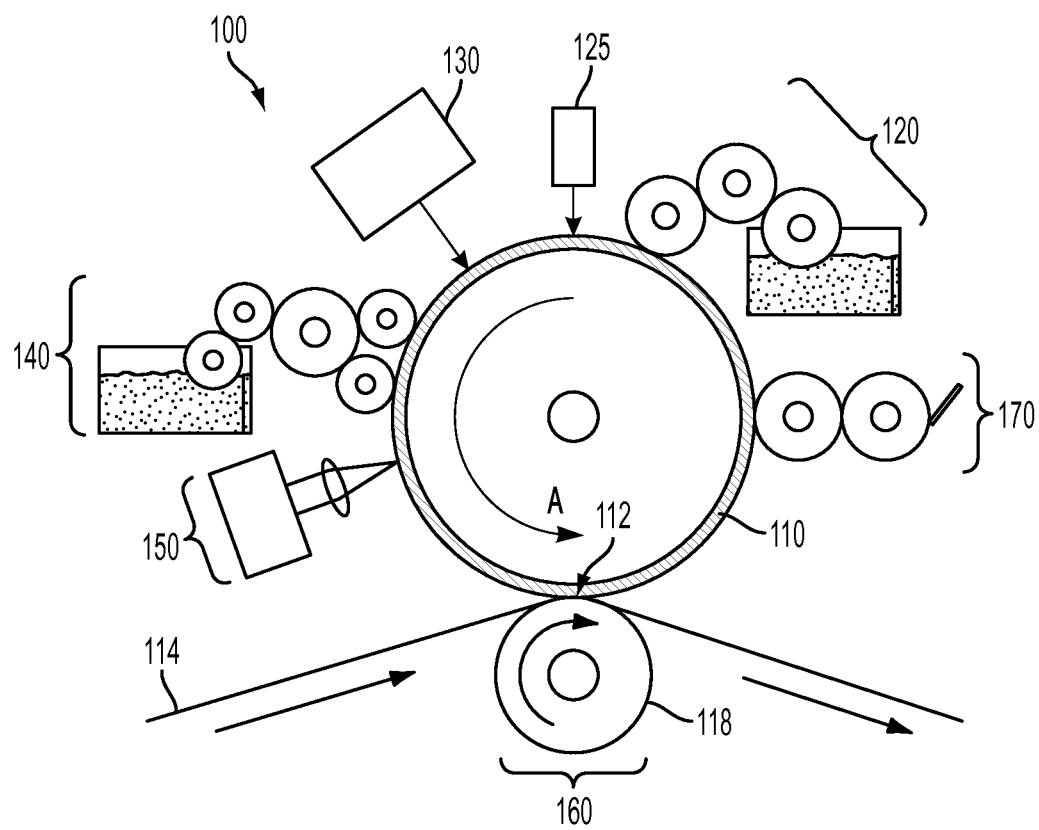
FIG. 1 shows a side diagrammatical view of a related art ink-based digital printing system.

Exemplary embodiments are intended to cover all alternatives, modifications, and equivalents as may be included within the spirit and scope of methods and systems as described herein.

The modifier "about" used in connection with a quantity is inclusive of the stated value and has the meaning dictated by the context (for example, it includes at least the degree of error associated with the measurement of the particular quantity). When used with a specific value, it should also be considered as disclosing that value.

Reference is made to the drawings to accommodate understanding of systems for ink-based digital printing using a system having an imaging member for which functionalized carbon black formed in accordance with methods of embodiments are useful, and methods of forming functionalized carbon black in accordance with embodiments. In the drawings, like reference numerals are used throughout to designate similar or identical elements.

Ink-based digital printing or variable data lithographic printing systems are discussed to provide an example of an advantageous use for functionalized carbon black formed by methods in accordance with embodiments. Functionalized carbon black compositions formed by methods of embodiments may be useful for other printing applications, and are particularly useful for ink-based digital printing applications because they may be uniformly dispersed in an imaging member surface layer to enable high speed, high quality ink-based digital printing. Ink-based digital printing systems are discussed by way of example. Inks in accordance with embodiments may also be suitable for other printing systems, such as those that include an intermediate transfer configuration, or toner printing and/or fusing systems.

"Variable data lithography printing," or "ink-based digital printing," or "digital offset printing" is lithographic printing of variable image data for producing images on a substrate that are changeable with each subsequent rendering of an image on the substrate in an image forming process. "Variable data lithographic printing" includes offset printing of ink images using lithographic ink wherein the images are based on digital image data that may vary from image to image. Ink-based digital printing uses a variable data lithography printing system, or digital offset printing system. A "variable data lithography system" is a system that is configured for lithographic printing using lithographic inks and based on digital image data, which may be variable from one image to the next.

Such systems are disclosed in U.S. patent application Ser. No. 13/095,714 ("714 application"), titled "Variable Data Lithography System," filed on Apr. 27, 2011, by Stowe et al., the disclosure of which is hereby incorporated by reference herein in its entirety. The systems and methods disclosed in the 714 application are directed to improvements on various aspects of previously-attempted variable data imaging lithographic marking concepts based on variable patterning of dampening fluids to achieve effective truly variable digital data lithographic printing.

The 714 application describes an exemplary variable data lithography system 100 for ink-based digital printing, such as that shown, for example, in FIG. 1. A general description of the exemplary system 100 shown in FIG. 1 is provided here. Additional details regarding individual components and/or subsystems shown in the exemplary system 100 of FIG. 1 may be found in the 714 application.

As shown in FIG. 1, the exemplary system 100 may include an imaging member 110. The imaging member 110 in the embodiment shown in FIG. 1 is a drum, but this exemplary depiction should not be interpreted so as to exclude embodiments wherein the imaging member 110 includes a drum, plate or a belt, or another now known or later developed configuration. The reimageable surface may be formed of materials including, for example, silicones, including polydimethylsiloxane (PDMS), FKMs among others. The reimageable surface may be formed of a relatively thin layer over a mounting layer, a thickness of the relatively thin layer being selected to balance printing or marking performance, durability and manufacturability.

The imaging member 110 is used to apply an ink image to an image receiving media substrate 114 at a transfer nip 112. The transfer nip 112 is formed by an impression roller 118, as part of an image transfer mechanism 160, exerting pressure in the direction of the imaging member 110. Image receiving medium substrate 114 should not be considered to be limited to any particular composition such as, for example, paper, plastic, or composite sheet film. The exemplary system 100 may be used for producing images on a wide variety of image receiving media substrates. The 714 application also explains the wide latitude of marking (printing) materials that may be used, including marking materials with pigment densities greater than 10% by weight. As does the 714 application, this disclosure will use the term ink to refer to a broad range of printing or marking materials to include those which are commonly understood to be inks, pigments, and other materials which may be applied by the exemplary system 100 to produce an output image on the image receiving media substrate 114.

The 714 application depicts and describes details of the imaging member 110 including the imaging member 110 being comprised of a reimageable surface layer formed over a structural mounting layer that may be, for example, a cylindrical core, or one or more structural layers over a cylindrical core.

The system 100 includes a dampening fluid system 120 generally comprising a series of rollers, which may be considered as dampening rollers or a dampening unit, for uniformly wetting the reimageable surface of the imaging member 110 with dampening fluid. A purpose of the dampening fluid system 120 is to deliver a layer of dampening fluid, generally having a uniform and controlled thickness, to the reimageable surface of the imaging member 110. As indicated above, it is known that a dampening fluid such as fountain solution may comprise mainly water optionally with small amounts of isopropyl alcohol or ethanol added to reduce surface tension as well as to lower evaporation energy necessary to support subsequent laser patterning, as will be described in greater detail below. Small amounts of certain surfactants may be added to the fountain solution as well. Alternatively, other suitable dampening fluids may be used to enhance the performance of ink based digital lithography systems. Exemplary dampening fluids include water, Novec 7600 (1,1,1,2,3,3-Hexafluoro-4-(1,1,2,3,3,3-hexafluoropropoxyl)pentane and has CAS#870778-34-0), and D4 (octamethylcyclotetrasiloxane). Other suitable dampening fluids are disclosed, by way of example, in co-pending U.S. patent application Ser. No. 13/284,114, filed on Oct. 28, 2011, titled DAMPENING FLUID FOR DIGITAL LITHOGRAPHIC PRINTING, the disclosure of which is hereby incorporated herein by reference in its entirety.

Once the dampening fluid is metered onto the reimageable surface of the imaging member 110, a thickness of the dampening fluid may be measured using a sensor 125 that may provide feedback to control the metering of the dampening fluid onto the reimageable surface of the imaging member 110 by the dampening fluid system 120.

After a precise and uniform amount of dampening fluid is provided by the dampening fluid system 120 on the reimageable surface of the imaging member 110, and optical patterning subsystem 130 may be used to selectively form a latent image in the uniform dampening fluid layer by image-wise patterning the dampening fluid layer using, for example, laser energy. Typically, the dampening fluid will not absorb the optical energy (IR or visible) efficiently. The reimageable surface of the imaging member 110 should ideally absorb most of the laser energy (visible or invisible such as IR) emitted from the optical patterning subsystem 130 close to the surface to minimize energy wasted in heating the dampening fluid and to minimize lateral spreading of heat in order to maintain a high spatial resolution capability. Alternatively, an appropriate radiation sensitive component may be added to the dampening fluid to aid in the absorption of the incident radiant laser energy. While the optical patterning subsystem 130 is described above as being a laser emitter, it should be understood that a variety of different systems may be used to deliver the optical energy to pattern the dampening fluid.

The mechanics at work in the patterning process undertaken by the optical patterning subsystem 130 of the exemplary system 100 are described in detail with reference to the 714 application's FIG. 5. Briefly, the application of optical patterning energy from the optical patterning subsystem 130 results in selective removal of portions of the layer of dampening fluid.

Following patterning of the dampening fluid layer by the optical patterning subsystem 130, the patterned layer over the reimageable surface of the imaging member 110 is presented to an inker subsystem 140. The inker subsystem 140 is used to apply a uniform layer of ink over the layer of dampening fluid and the reimageable surface layer of the imaging member 110. The inker subsystem 140 may use an anilox roller to meter an offset lithographic ink onto one or more ink forming rollers that are in contact with the reimageable surface layer of the imaging member 110. Separately, the inker subsystem 140 may include other traditional elements such as a series of metering rollers to provide a precise feed rate of ink to the reimageable surface. The inker subsystem 140 may deposit the ink to the pockets representing the imaged portions of the reimageable surface, while ink on the unformatted portions of the dampening fluid will not adhere to those portions.

The cohesiveness and viscosity of the ink residing in the reimageable layer of the imaging member 110 may be modified by a number of mechanisms. One such mechanism may involve the use of a rheology (complex viscoelastic modulus) control subsystem 150. The rheology control system 150 may form a partial crosslinking core of the ink on the reimageable surface to, for example, increase ink cohesive strength relative to the reimageable surface layer. Curing mechanisms may include optical or photo curing, heat curing, drying, or various forms of chemical curing. Cooling may be used to modify rheology as well via multiple physical cooling mechanisms, as well as via chemical cooling.

The ink is then transferred from the reimageable surface of the imaging member 110 to a substrate of image receiving medium 114 using a transfer subsystem 160. The transfer occurs as the substrate 114 is passed through a nip 112 between the imaging member 110 and an impression roller 118 such that the ink within the voids of the reimageable surface of the imaging member 110 is brought into physical contact with the substrate 114. With the adhesion of the ink having been modified by the rheology control system 150, modified adhesion of the ink causes the ink to adhere to the substrate 114 and to separate from the reimageable surface of the imaging member 110. Careful control of the temperature and pressure conditions at the transfer nip 112 may allow transfer efficiencies for the ink from the reimageable surface of the imaging member 110 to the substrate 114 to exceed 95%. While it is possible that some dampening fluid may also wet substrate 114, the volume of such a dampening fluid will be minimal, and will rapidly evaporate or be absorbed by the substrate 114.

In certain offset lithographic systems, it should be recognized that an offset roller, not shown in FIG. 1, may first receive the ink image pattern and then transfer the ink image pattern to a substrate according to a known indirect transfer method.

Following the transfer of the majority of the ink to the substrate 114, any residual ink and/or residual dampening fluid must be removed from the reimageable surface of the imaging member 110, preferably without scraping or wearing that surface. An air knife may be employed to remove residual dampening fluid. It is anticipated, however, that some amount of ink residue may remain. Removal of such remaining ink residue may be accomplished through use of some form of cleaning subsystem 170. The 714 application describes details of such a cleaning subsystem 170 including at least a first cleaning member such as a sticky or tacky member in physical contact with the reimageable surface of the imaging member 110, the sticky or tacky member removing residual ink and any remaining small amounts of surfactant compounds from the dampening fluid of the reimageable surface of the imaging member 110. The sticky or tacky member may then be brought into contact with a smooth roller to which residual ink may be transferred from the sticky or tacky member, the ink being subsequently stripped from the smooth roller by, for example, a doctor blade.

The 714 application details other mechanisms by which cleaning of the reimageable surface of the imaging member 110 may be facilitated. Regardless of the cleaning mechanism, however, cleaning of the residual ink and dampening fluid from the reimageable surface of the imaging member 110 is essential to preventing ghosting in the proposed system. Once cleaned, the reimageable surface of the imaging member 110 is again presented to the dampening fluid system 120 by which a fresh layer of dampening fluid is supplied to the reimageable surface of the imaging member 110, and the process is repeated.

The imaging member reimageable surface may comprise a polymeric elastomer, such as silicone rubber and/or fluorosilicone rubber or FKMs such as Viton GF from DuPont or P959 from Solvay Solexis, for example. The term "silicone" is well understood in the art and refers to polyorganosiloxanes having a backbone formed from silicon and oxygen atoms and sidechains containing carbon and hydrogen atoms. For the purposes of this application, the term "silicone" should also be understood to exclude siloxanes that contain fluorine atoms, while the term "fluorosilicone" is used to cover the class of siloxanes that contain fluorine atoms. Other atoms may be present in the silicone rubber, for example nitrogen atoms in amine groups which are used to link siloxane chains together during crosslinking. The side chains of the polyorganosiloxane can also be alkyl or aryl.

A "fluoroelastomer" is a fluorocarbon-derivative, a synthetic rubber. The term fluoroelastomer is well understood in the art. A fluoroelastomer or fluoro rubber of the polymethylene type uses vinylidene fluoride as a comonomer and has substituent fluoro, alkyl, perfluoroalkyl, or perfuoroalkoxy groups on the polymer chain. Fluoroelastomers are categorized under the ASTM D1418, and have the ISO 1629 designation FKM. This class of elastomer is a family comprising copolymers of hexafluoropropylene (HFP) and vinyldiene fluoride (VDF or VF2), terpolymers of tetrafluoroethylene (TFE), vinyldiene fluoride (VDF) and hexafluoropropylene (HFP) and perfluoromethylvinylether (PMVE) containing components. Exemplary fluoroelastomers are commercially available from DuPont Performance Elastomers L.L.C. under the VITON brand, and from Solay under the TECNOFLON brand as P959.

The term "alkyl" as used herein refers to a group composed entirely of carbon atoms and hydrogen atoms that is fully saturated. The alkyl group may include a chain that is linear, branched, or cyclic. For example, linear alkyl radicals generally have the formula $.C_nH_{2n+1}$.

The term "aryl" refers to an aromatic group composed entirely of carbon atoms and hydrogen atoms. When aryl is described in connection with a numerical range of carbon atoms, it should not be construed as including substituted aromatic radicals.

The term "alkoxy" refers to an alkyl group singular bonded to an oxygen atom.

The term "amino" refers to a group containing a nitrogen atom attached by single bonds to hydrogen atoms, alkyl groups, aryl groups, or a combination thereof. An "amine" is an organic compound that contains an amino group. Amines are derivates of the inorganic compound ammonia.

Methods in accordance with embodiments include functionalizing carbon black with amino-terminated fluoropolymers, e.g., fluorosilicones, to yield a uniform and stable dispersion in a fluorosilicone matrix or in a FKM matrix. In an embodiment, the carbon black particles are chemically modified with amino-functionalized fluorosilicone, such as amino-terminated F-PDMS ("EF"), or other similar compounds, by the formation of amide bonds between surface carboxylic groups of CB particles and amino groups of the EF and a coupling agent such as N,N'-dicyclohexylcarbodiimide (DCC).

Amino-functionalized carbon black was produced using methods in accordance with an embodiment. Carbon black particles, available as Orion L6 carbon black from Printex L6 carbon black from Orion Engineered Carbons were oxidized with concentrated nitric acid, $HNO_3$, to increase the concentration of carboxylic groups on the surface of the carbon black particles and cause the surface to be more reactive. Then, EF was chemically grafted to the carboxylic groups of the carbon black particles by way of amide bonds. The functionalization was confirmed by x-ray photoelectron spectroscopy ("XPS").

The resulting dispersions were very stable in the trifluorotoluene ("TFT") for days. The optical microscopy showed that when the functionalized carbon black is added to the fluorosilicone matrix, very uniform and small particle size dispersion (at least about 500 nm or less) resulted in comparison with 1-5 micron aggregates and non-uniform dispersion found in related art unmodified carbon black particles. This is particularly important because it enables tailoring electrical and mechanical properties of filled systems at lower loadings. This enables lower power lasers, higher printing speed and better image resolution for ink-based digital printing systems such as those shown in FIG. 1, for example.

Figure 2:
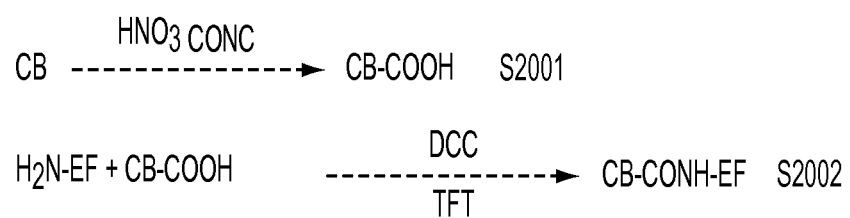
FIG. 2 shows a synthesis mechanism for forming a functionalized carbon black composition in accordance with an exemplary embodiment.

FIG. 2 shows methods for forming functionalized carbon black in accordance with an exemplary embodiment. A product of carbon black functionalization in accordance with methods of embodiments may include a carbon black molecule having a functional group selected from at least of an acid moiety, and/or may include addition of alcohol, ketone, and quinone groups. Functionalized carbon black samples formed in accordance with methods were characterized using XPS, and the data is presented Table 1. The data shown in Table 1 indicates presence of nitrogen and fluorine in EF modified carbon black, which indicates the functionalization of carbon black with EF by way of the amide bond.

TABLE 1

XPS Data

|  | C (at %) | N (at %) | O (at %) | F (at %) | Si (at %) | S (at %) |
|---|---|---|---|---|---|---|
| Carbon Black I | 98.53 | 0.00 | 1.31 | 0.00 | 0.00 | 0.16 |
| Carbon Black HNO3 II | 96.14 | 0.00 | 3.72 | 0.00 | 0.00 | 0.14 |
| Carbon Black EF III | 83.14 | 3.04 | 7.67 | 3.57 | 2.53 | 0.06 |

As shown in FIG. 2, methods may include mixing carbon black with concentrated nitric acid at S2001. Nitric acid may be mixed with carbon black for seven hours at room temperature to oxidize the carbon black and increase an amount carboxylic acid groups on a surface of the carbon black particle. The oxidized carbon black may be repeatedly washed in deionized water using an ultracentrifuge until a pH of the carbon black solution is around 5. The carbon black may be dried using a vacuum at 150 degrees Celsius for one hour.

Then, EF is added to the functionalized carbon black molecule with DCC in the presence of trifluorotoluene ("TFT") at S2002 whereby EF is chemically grafted to the carboxylic group(s) of the carbon black particle to form carbon black having an amino-functionalized fluorosilicone functional group. In particular, oxidized carbon black may be added to TFT, followed by addition of EF and DCC. The resulting mixture may be stirred overnight, and subsequently washed with TFT and processed using an ultracentrifuge to remove residual EF and DCC. TFT byproducts may be evaporated using a vacuum oven. The product functionalized carbon black may be redispersed in TFT, for example. The functionalized carbon black samples that were tested to produce the data shown in Table 1 were formed using 0.726 g of carbon black, 10 g of TFT, and 1 g of DCC.

Exemplary EF compounds may include aminoterminated fluorinated polydimethylsiloxane (PDMS). PDMS or dimethicone is a mineral-organic polymer (a structure containing carbon, silicon and oxygen) of the siloxane family that is readily available. The chemical formula for PDMS is $CH_3[Si(CH_3)_2O]_nSi(CH_3)_3$, where n is the number of repeating monomer $SiO(CH_3)_2$] units. Alternatively, other exemplary fluoropolymers including poly(vinylmethyl)siloxane (PVMS) may comprise the aminoterminated fluoropolymer that may be used to form aminofunctionalized carbon black in accordance with provided methods.

Figure 3:
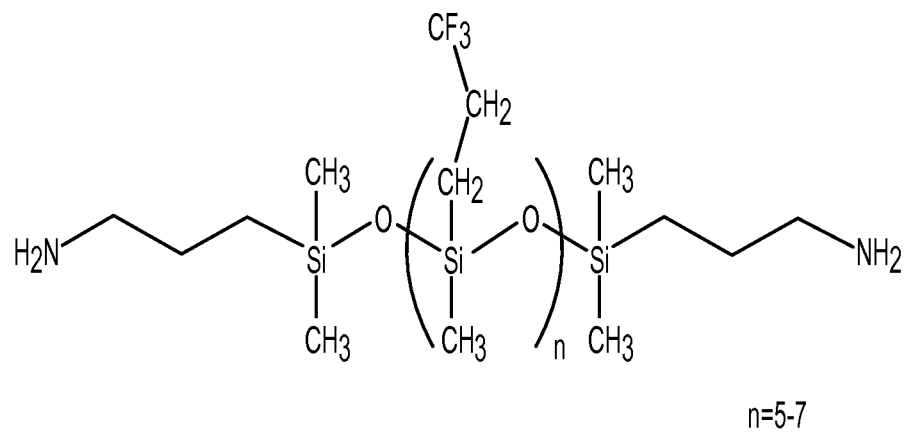
FIG. 3 shows a structural formula of a amino-terminated F-PDMS molecule.

FIG. 3 shows a chemical structure of amino-terminated F-PDMS, which may comprise the EF component used in methods of embodiments. Amino-terminated F-PDMS having the structure shown in FIG. 3 is known and readily available from, for example, Wacker Chemie AG.

Figure 4A:
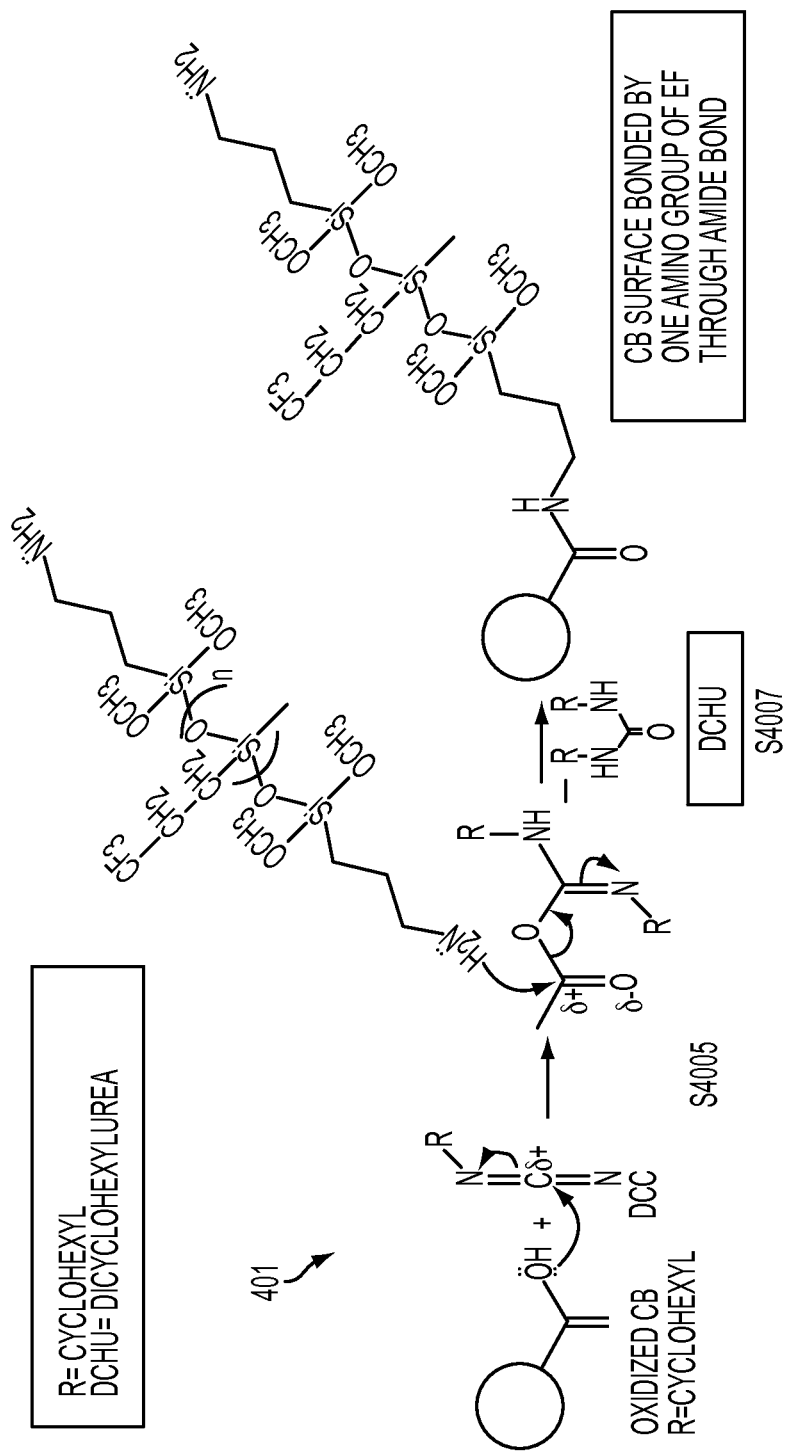
FIG. 4A shows methods for forming a functionalized carbon black and a first potential product in accordance with an exemplary embodiment.

Methods for forming functionalized carbon black in accordance with embodiments may work in accordance with the reaction mechanism shown in FIG. 4A. In particular, FIG. 4A shows a possible reaction mechanism of functionalization of carbon black. In particular, FIG. 4A shows oxidized carbon black being combined with DCC at S4005. The product molecule is caused to react with an EF molecule at S4007, yielding DCHU as a byproduct, and amino-terminated functionalized carbon black. The functionalized carbon black product shown in FIG. 4A includes a surface being bonded by a single amino group of the EF by way of an amide bond.

Figure 4B:
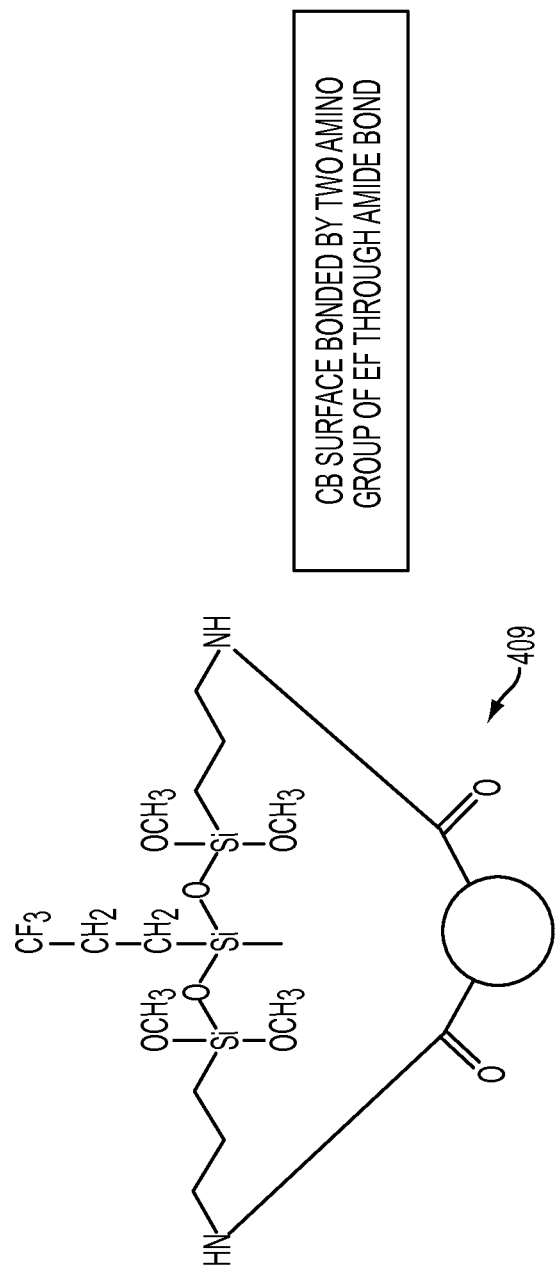
FIG. 4B shows a second potential product.

The product shown in FIG. 4A is believed to be an energetically favorable product because the reaction pathway yields excess EF. A second potential product is shown in FIG. 4B. The second potential product includes a surface of carbon black bonded by two amino groups of an EF molecule by way of amide bonds.

The modified carbon black prepared for producing the results shown in Table 1 were further dispersed in fluorosilicone and an optical microscopy was carried out to check a quality of dispersion in unmodified carbon black and EF-modified carbon black. An optical micrograph showing unmodified carbon black dispersed in fluorosilicone was compared with a micrograph of EF-functionalized carbon black in fluorosilicone. The results showed that unmodified carbon black, which tended to agglomerate with 1-5 micron or higher aggregates, did not uniformly disperse in the solution. Contrarily, EF functionalized carbon black was uniformly distributed, and no aggregates were observed using an optical microscope. As such, a size of agglomerates was found to be less than 500 nanometers.

It will be appreciated that the above-disclosed and other features and functions, or alternatives thereof, may be desirably combined into many other different systems or applications. Also, various presently unforeseen or unanticipated alternatives, modifications, variations or improvements therein may be subsequently made by those skilled in the art.

What is claimed is:

1. A method for forming functionalized carbon black useful for uniform dispersion in a surface material of printing system components, comprising:
    providing carbon black;
    providing a fluoropolymer having a terminal amino group; and
    mixing the amino-terminated fluoropolymer and the carbon black, wherein in the fluoropolymer is amino-terminated PDMS;
    providing nitric acid;
    mixing the carbon black with the nitric acid to oxidize a surface of the carbon black whereby oxidized carbon black is formed;

washing the oxidized carbon black with deionized water until a pH of the carbon black in solution is 5;

drying the carbon black using vacuum at 150 degrees Celsius for one hour;

the mixing the amino-terminated fluoropolymer and the carbon black further comprising the carbon black being the vacuum dried, oxidized carbon black, the amount of dried, oxidized carbon black lying in a range of 0.5 g to 1.0 g, the amount of amino-terminated fluoropolymer being 10 g, and an amount of the coupling agent being 1 g.

2. The method of claim 1, comprising:

providing a coupling agent for the mixing.

3. The method of claim 2, wherein the coupling agent is N,N'-dicyclohexylcarbodiimide.

4. The method of claim 1, wherein the mixing carbon black with the nitric acid comprises mixing for seven hours.

5. The method of claim 1, wherein the mixing carbon black with the nitric acid comprises mixing at room temperature.

6. The method of claim 1, comprising:

mixing trifluorotoluene with the dried, oxidized carbon black before adding the amino-terminated fluoropolymer to the carbon black and the coupling agent.

7. The method of claim 6, comprising:

washing the functionalized carbon black with trifluorotoluene for removing residual EF and/or coupling agent; and evaporating the trifluorotoluene after the washing.

8. The method of claim 7, comprising the washing being conducted using an ultracentrifuge.

9. The method of claim 7, comprising the evaporating being conducted using a vacuum oven.

10. A method for forming an imaging member having a functionalized carbon black filler component in a surface thereof, comprising:

providing carbon black;

providing a fluoropolymer having a terminal amino group; and mixing the amino-terminated fluoropolymer and the carbon black, wherein in the fluoropolymer is amino-terminated PDMS;

providing nitric acid;

mixing the carbon black with the nitric acid to oxidize a surface of the carbon black whereby oxidized carbon black is formed;

washing the oxidized carbon black with deionized water until a pH of the carbon black in solution is 5;

drying the carbon black using vacuum at 150 degrees Celsius for one hour;

the mixing the amino-terminated fluoropolymer and the carbon black further comprising the carbon black being the vacuum dried, oxidized carbon black, the amount of dried, oxidized carbon black lying in a range of 0.5 g to 1.0 g, the amount of amino-terminated fluoropolymer being 10 g, and an amount of the coupling agent being 1 g.

* * * * *